United States Patent [19]

Narayanan

[11] Patent Number: 5,317,042
[45] Date of Patent: * May 31, 1994

[54] WATER-BASED MICROEMULSION FORMULATIONS

[75] Inventor: Kolazi S. Narayanan, Palisades Park, N.J.

[73] Assignee: ISP Investments Inc., Wilmington, Del.

[*] Notice: The portion of the term of this patent subsequent to Apr. 5, 2011 has been disclaimed.

[21] Appl. No.: 953,331

[22] Filed: Sep. 30, 1992

Related U.S. Application Data

[63] Continuation-in-part of Ser. No. 654,250, Feb. 12, 1991, abandoned, which is a continuation-in-part of Ser. No. 546,014, Jun. 28, 1990, Pat. No. 5,156,666, which is a continuation-in-part of Ser. No. 505,030, Apr. 5, 1990, Pat. No. 5,160,528, which is a continuation-in-part of Ser. No. 448,707, Dec. 11, 1989, Pat. No. 5,071,463.

[51] Int. Cl.$^5$ ............... A01N 25/00; A01N 65/00; A01N 37/08
[52] U.S. Cl. .................. 514/772; 514/788; 514/65; 514/572; 514/937
[58] Field of Search ............. 514/788, 938, 937, 941, 514/772, 772.3, 65, 572; 71/79, 93; 504/116

[56] References Cited

U.S. PATENT DOCUMENTS 4,840,663  6/1989  Quadranti et al. ............ 71/93

OTHER PUBLICATIONS

Chemical Abstracts (109: 131269m) 1988).

Primary Examiner—Frederick E. Waddell
Assistant Examiner—K. Weddington
Attorney, Agent, or Firm—Walter Katz; Marilyn J. Maue; Joshua J. Ward

[57] ABSTRACT

Clear, stable, efficacious, aqueous microemulsions of a pyrethroid insecticide, optionally with another agriculturally active ingredient, are provided herein. The aqueous microemulsions are obtained by providing an inert matrix composition containing a defined mixture of nonionic surfactants, optionally including an anionic surfactant, mixing with a pyrethroid to form a microemulsion concentrate, and diluting with water. Preferably, the aqueous microemulsion includes an N-alkyl ($C_1$–$C_4$) pyrrolidone therein as a cosolvent in the microemulsion system.

11 Claims, No Drawings

WATER-BASED MICROEMULSION FORMULATIONS

CROSS-REFERENCE TO RELATED U.S. PATENT APPLICATIONS

This application is a continuation-in-part of application Ser. No. 654,250, filed Feb. 12, 1991; now abandoned which, in turn, is a continuation-in-part of application Ser. No. 546,014, filed Jun. 28, 1990, now U.S. Pat. No. 5,156,666, which, in turn, is a continuation-in-part of application Ser. No. 505,030, filed Apr. 5, 1990, now U.S. Pat. No. 5,160,528 which, in turn, is a continuation-in-part of application Ser. No. 448,707, filed Dec. 11, 1989 (now U.S. Pat. No. 5,071,463), (hereinafter, collectively referred to as the Parent Applications) the contents of all of which are incorporated herein by reference.

BACKGROUND OF THE INVENTION

1. Field of the Invention

The invention relates to a delivery system for agriculturally active chemicals, and, more particularly, to an inert matrix composition for forming a microemulsion concentrate and an aqueous microemulsion of a pyrethroid insecticide.

2. Definitions

As used herein, the following terms have the meanings indicated:

(a) "Microemulsion" means an oil-in-water or water-in-oil, transparent thermodynamically stable dispersion of two or more immiscible liquids wherein the dispersed phase consists of small droplets with diameters in the range of about 10 to 100 millimicrons. Such microemulsions are clear and contain at least about 80% by weight water.

(b) "Macroemulsion" means an emulsion of water-in-oil or oil-in-water wherein the interior phase is in the form of visually discernable droplets and the overall emulsion is cloudy, and wherein the droplet diameter is greater than about 100 millimicrons.

(c) "Clear" or "Transparent" as applied to a microemulsion means that the composition appears as a single phase without any particulate or colloidal material or a second phase being present when viewed by the naked eye.

(d) "Substantially Insoluble" or "Insoluble" means that for all practical purposes, the solubility of the compound in water is insufficient to make the compound practicably usable in an agricultural end use without some modification either to increase its solubility or dispersability in water, so as to increase the compound's bioavailability or avoid the use of excessively large volumes of solvent.

(e) "High Degree of Loading" in a microemulsion concentrate means an agriculturally active ingredient content of at least about 5 percent by weight.

(f) The term "Agriculturally Active Chemical or Ingredient" (AAC) means compounds and mixtures thereof which can be used as agricultural fertilizers, nutrients, plant growth accelerants, herbicides, plant growth controlling chemicals, and chemicals which are effective in killing plants, insects, microorganisms, fungi, bacteria and the like which are commonly referred to as insecticides, bactericides, fungicides, nematocides, fumigants, synergists, i.e., compounds which when used in conjunction with other AAC's enhance their activity and the like, as well as any other chemicals having properties which are suitable for agricultural uses in terms of application to plants or domestic uses for controlling insects and pests.

(g) "Synthetic Pyrethroid" is an AAC such as organic compounds having the formulas:

($\pm$) alpha-cyano-3-phenoxybenzyl ($\pm$) cis, trans 3-(2,2-dichlorovinyl)-2,2-dimethyl cyclopropane carboxylate;

(RS)-3-allyl-2-methyl-4-oxocyclopent-2-enyl (1RS)-cis, trans-chrysanthemate;

3-phenoxybenzyl (1RS)-cis, trans-3-(2,d-dichlorovinyl)-2,2-dimethylcyclopropanecarboxylate;

3,4,5,6-tetrahydrophthalimidomethyl ($\pm$)-cis, transchrysanthemate);

5-[2-(2-*butoxyethoxy)ethoxymethyl]-6-propyl-1,3-benzodioxole;

* this compound is a known synergist for synthetic pyrethroids (RS)-alpha-cyano-3-phenoxybenzyl 2,2,3,3-tetramethylcyclopropanecarboxylate; and ($\pm$) cyano (3-phenoxyphenyl methyl ($\pm$)-4-(difluoromethyoxy) alpha-(1-methylethyl) benzene acetate.

Commercial synthetic pyrethroid insecticides include D-allethrin, permethrin, tetramethrin and kathon, alone, or as complex mixtures, with and without synergists, such as piperonyl butoxide**, or other AAC ingredients, such as 2N-octyl-4-isothiazdin-3-one and propaconazole.

** 3,4-methylenedioxy-6-propyl benzyl n-butyl diethylene glycol ether (h) "Inert Matrix Composition" (IMC)—a predetermined mixture of defined nonionic surfactants, optionally with one or more anionic surfactants, and/or with a $C_1$-$C_4$ alkylpyrrolidone, e.g. N-methylpyrrolidone, which, upon admixture with a pyrethroid insecticide and water, will form a clear, efficacious, aqueous microemulsion which is stable at or below room temperature for an extended period of time.

(i) "Two-Part Microemulsion System" (TPMS)—as the first part, the IMC; as the second part, a pyrethroid insecticide; and, wherein, optionally, up to 60% by weight of a $C_1$-$C_4$ alkylpyrrolidone, e.g. N-methylpyrrolidond, is present in said system as a component of either or both of said parts before admixture.

(j) "Microemulsion Concentrate" (MEC)—the admixture product of both parts of the TPMS.

(k) "Water-Based Microemulsion" (WBME) or "Aqueous Microemulsion" (AM)—The TPMS (0.5–20%) and water (80–99.5%), by weight.

(l) "Nonionic Surfactant" - Representative materials include:

(1) N-Alkylpyrrolidone (alkyl $C_6$-$C_{18}$), e.g. N-octylpyrrolidone - (Surfadone LP-100 - ISP)

(2) Ethylene oxide (EO)/propylene oxide (PO)/EO block copolymers, e.g. (2 EO/16 PO/2 EO—$H_2O$) - (Pegal L-31), and (3) Alkylphenol ethoxylated alcohol having an HLB$\geq$6, e.g. nonylphenol ethoxylated alcohol with 9 EOs - (Igepal CO-630).

(m) "Anionic Surfactant" — Representative materials include: Nonylphenol ethoxylated phosphate ester with 9 EOs Gafac RE-610.

(n) "Cosolvent" — An N-alkyl ($C_1$-$C_4$) pyrrolidone — representative materials include: N-Methylpyrrolidone (NMP).

DESCRIPTION OF THE PRIOR ART

Agriculturally active chemicals are most preferably applied in the form of aqueous emulsions, solutions, or suspensions. Occasionally, they may also be applied in the form of a dust wherein the active ingredient is adsorbed onto or mixed with a finely divided inert carrier material, such as, china clay, or the like. With such powdered or dust compositions, drift due to wind is a problem and consequently, liquid formulations are preferred.

One of the problems with such liquid formulations is the fact that chemicals having agricultural activity often exhibit extreme insolubility in water. This results in their having to be dissolved either in organic solvents or utilized in the form of emulsions or suspensions. With respect to the use of organic solvents, these are generally disadvantageous from an environmental and cost viewpoint. Particularly, such organic chemicals may exhibit toxicity or side-effects which may be adverse to the effect of the agricultural chemical itself or to the subsequent fruit or vegetable produced in the particular agricultural use. This toxicity may also be disadvantageous with respect to handling.

When attempts are made to provide emulsified or suspension formulations, difficulties are encountered with respect to providing a desirably high concentration of the agriculturally active ingredient. Thus, when such agriculturally active chemicals are formulated into a macroemulsion (sometimes referred to herein as an emulsion), it is difficult to maintain the emulsified state. This, in turn, creates problems in maintaining a uniform formulation, particularly, when the formulation is diluted with water for application to the plants.

An attempt to provide concentrates of agriculturally useful chemicals for producing macroemulsions was disclosed in South African Patent Application No. 695,393, filed Jul. 25, 1969. This application was directed to the formulation of a concentrate substantially water-insoluble pesticides for agricultural use. The pesticides, either in oil or solid form, were mixed with pyrrolidones having a hydrogen or a lower alkyl group containing from 1 to 4 carbon atoms attached to the nitrogen atom of the pyrrolidone ring. The application disclosed that concentrated solutions of difficult to dissolve pesticides could be formulated and that such concentrates exhibited good stability. The concentrates utilized were those containing the pesticidal active ingredient, the particular lower alkyl pyrrolidone, a co-solvent which is usually a common organic solvent, such as, an aromatic including xylene, methylated and polyalkylated naphthalenes and aliphatic solvents, and a dispersing or emulsifying agent, such as, a surfactant, including polyoxyethylene alkylphenols, polyoxyethylene fatty esters, polyoxyethylene sorbitan fatty esters which may be blended with oil-soluble sulfonates, calcium and aminosulfonate salts, and the like.

However, this prior art did not offer a solution to the problem arising from the difficulty in maintaining the stability of the emulsion formed after the concentrate was diluted with water. Consequently, unless the diluted form of the concentrate was used immediately after emulsification, it was difficult to provide a stable diluted formulation for application to the plants, soil, pests, and the like.

In addition, for such agricultural uses, it is also desirable to avoid the use of toxic solvents, including those of Lists 1 and 2 of 40 C.F.R. 154.7 dated Apr. 22, 1987, which includes inerts of toxicological concern and solvents having high flash points, as well as to increase the amount of the agriculturally active material in the concentrate. Moreover, many organic solvents which have been used in the past, even those exhibiting relatively low toxicities, are not biodegradable and thus remain as a pollutant.

The Parent Applications referred to hereinabove have provided solutions to the problem of providing stable macroemulsions of insoluble agricultural chemicals in aqueous systems. This was accomplished by the use of long and short chain alkyl lactams for formation of emulsifiable concentrates of agricultural chemicals. Also see U.S. Pat. application Ser. No. 257,596, filed Oct. 14, 1988, (now U.S. Pat. No. 5,093,031), the contents of which are incorporated herein by reference, which disclosed the use of long chain alkyl lactams to prepare emulsifiable concentrates of agriculturally active ingredients, e.g., herbicides, fungicides, pesticides, and the like, which on dilution with water, formed stable macroemulsions.

While these patent applications disclose the preparation of emulsions of a wide variety of agriculturally active chemicals which are normally highly insoluble in water, the emulsions produced from all of these prior art concentrates are macroemulsions. The macroemulsions which result from their dilution with water, while relatively stable, may, at some point in time, settle out into two phases or more.

It is desirable, however, to provide compositions which will deliver effective amounts of insoluble agriculturally active compound which exhibit improved stability with respect to the emulsion. In addition, it is desired to provide increased chemical stability for such agricultural compounds. Thus, certain agricultural compounds, notably, insecticides, are relatively chemically unstable in water and tend to hydrolyze after a short period of time. As a result, even short periods of increased chemical stability for such compounds are advantageous.

It is also desirable to increase the efficacy of a given agricultural compound relative to its loading content. It has been theorized that microemulsions can improve the efficacy of agriculturally active compounds relative to equivalent levels of the same compound in a macroemulsion composition. see Skelton, P. R., Munk, B. H., and Collins, H. M., "Formulation of Pesticide Microemulsions", *Pesticide Formulations and Application Systems;* 8th Volume, ASTM STP 980, D. A. Hovde and G. B. Beestman, Eds., American Society for Testing and Materials, Philadelphia, 1988. See also U.S. Pat. No. 3,954,967, and Canadian Patent 1025687. For a discussion of microemulsions, see *Microemulsions, Theory and Practice,* Leon M. Prince, Academic Press, (1977); and "Microemulsions-Properties Novel Chemistry", BH Robinson, chemistry in Britain 26 (1990), page 342.

SUMMARY OF THE INVENTION

Clear, stable, efficacious, aqueous microemulsions of a pyrethroid insecticide, alone, or in a complex mixture, with and without a synergist, or another active agricultural ingredient, are obtained by mixing the insecticide with an inert matrix composition containing a defined mixture of nonionic surfactants, optionally including an anionic surfactant, to form a microemulsion concentrate, and diluting with water. The aqueous microemulsion herein preferably includes an N-alkyl ($C_1$–$C_4$) pyrrolidone, which may be present as part of the inert matrix composition, or as a solvent for the pyrethroid, or in both.

DETAILED DESCRIPTION OF THE INVENTION

In accordance with the invention, the Inert Matrix Composition (IMC) comprises a predetermined mixture of nonionic surfactants, particularly a $C_6$-$C_{18}$ alkyl pyrrolidone, an ethylene oxide (EO)/propylene oxide (PO)/ethylene oxide (EO) block copolymer, and an alkyl phenol ethoxylated alcohol having an HLB≧6, e.g. nonylphenol ethoxylated alcohol with 9 EOs, in a weight ratio of about 0.5-2:0.5-2:3-12, respectively. The IMC optionally can contain up to 60% by weight of an N-alkyl ($C_1$-$C_4$) pyrrolidone, e.g. N-methylpyrrolidone.

The Two-Part Microemulsion System (TPMS) comprises, as one part, the IMC, and, as a second part, the pyrethroid, wherein the N-methylpyrrolidone cosolvent optionally may be present herein as a solvent for the pyrethroid; and the system includes up to 60% by weight of N-methylpyrrolidone.

The Microemulsion Concentrate (MEC) is obtained by mixing both parts of the TPMS to provide a suitable concentration of about 0.5-20 parts of the pyrethroid and about 80-99.5% parts of the TPMS.

The MEC may be stored, or diluted with water and stored until use, or diluted with water just before use. Upon dilution of the MEC with water, a Water Based Microemulsion (WBME), or simply, an Aqueous Microemulsion (AM), is formed, which contains from a few ppm to about 2% by weight of the pyrethroid. Generally, water is present in the aqueous microemulsion in an amount of about 80-99.5% by weight.

The end-use aqueous microemulsion system of pyrethroids herein is uniquely thermodynamically stable, has low toxicity and is biodegradable, and has wide, applicability with minor modifications of the ratio of its components. The system has very low turbidity (≦20 NTU at 10°-25° C.), and is thermally stable (45° C., 6 months). Turbidity is increased with temperature (900 NTU at 45° C.), but becomes clear when cooled to ambient temperature.

EXPERIMENTAL PROCEDURES AND RESULTS

The aqueous microemulsions (AM) of the invention were prepared by alternate procedures (a) and (b) which are described below.

Procedure (a)

The IMC was prepared by mixing predetermined amounts of defined nonionic surfactants, optionally with an anionic surfactant, and/or NMP. Then the pyrethroid insecticide was added and the mixture was shaken until the pyrethroid insecticide dissolved or the mixture became homogeneous, typically in about 30 minutes, which resulted in formation of an MEC. Then the MEC was diluted with a predetermined amount of water to form the AM. Water for dilution was either deionized water or WHO standard hard water (342 ppm as $CaCO_3$ equivalent).

Procedure (b)

The IMC was added to a pyrethroid insecticide dissolved in N-methylpyrrolidone to form the MEC, and water was added to form the WBME.

The aqueous microemulsion compositions of the invention made according to procedures (a) and (b) are summarized in TABLES 1 and 2 below, wherein the component amounts are in grams.

The invention will now be described with reference to the following examples.

TABLE 1

| | EXAMPLES | | | | | | |
|---|---|---|---|---|---|---|---|
| | A | B | C | D | E | F | G |
| Insert Matrix Composition | | | | | | | |
| N-Octylpyrrolidone | 0.25 | 1.25 | 0.375 | 0.5 | 0.25 | 0.875 | 1.16 |
| Pegol L-31 | 0.25 | 1.25 | 0.375 | 0.5 | 0.25 | 0.875 | 2.7 |
| Igepal CO-630 | 1.50 | 7.50 | 2.25 | 3.0 | 1.50 | 5.25 | 0.3 |
| N-Methylpyrrolidone | 1.0 | 0 | 1.0 | 1.0 | 2.5 | 2.7 | 1.088 |
| Microemulsion Concentrate | | | | | | | |
| Permethrin | 0.5 | 0.5 | 0.5 | 0.5 | 0.30 | 0.30 | 0.30 |
| Piperonyl Butoxide | — | — | — | — | — | — | — |
| Kathon 893* | — | — | — | — | 0.20 | — | — |
| Wocosin 50TK** | — | — | — | — | — | 1.0 | 1.0 |
| Water-Based Microemulsion | | | | | | | |
| Water | 96.5 | 89.5 | 95.5 | 94.5 | 95.0 | 89.0 | 93.5 |
| | 100 | 100 | 100 | 100 | 100 | 100 | 100 |
| Properties of Aqueous Microemulsion | | | | | | | |
| at RT | clear | clear | clear | clear | | | |
| at 0° C. | | | | | | | |
| 0 hr. | clear | clear | clear | clear | | | |
| 24 hr. | cloudy | clear | clear | clear | | | |
| 5 days | milky | clear | solid | clear | | | |
| upon warming to 450 and for 3 storing days | clear | clear | clear | | | | |
| cooling to RT | cloudy to clear | | | | | | |

*2N-octyl-4-isothiazolin-3-one
**50% solution of propaconazole in propylene glycol

TABLE 2

| | H | I | J | K | L | M | N | O |
|---|---|---|---|---|---|---|---|---|
| Insert Matrix Composition | | | | | | | | |
| N-Octylpyrrolidone | 0.625 | 0.625 | 0.625 | 0.625 | 0.625 | 0.625 | 0.625 | 0.375 |

TABLE 2-continued

| | H | I | J | K | L | M | N | O |
|---|---|---|---|---|---|---|---|---|
| Pegol L-31 | 0.625 | 0.625 | 0.625 | 0.625 | 0.625 | 0.625 | 0.625 | 0.375 |
| Igepal CO-630 | 3.75 | 3.75 | 3.75 | 3.75 | 3.75 | 3.75 | 3.75 | 2.25 |
| N-Methylpyrrolidone | 0.5 | 10 | 5.0 | 1.8 | 10 | 5 | 2.5 | 2.5 |
| Microemulsion Concentrate | | | | | | | | |
| Permethrin | 0.5 | — | — | — | 0.15 | 0.15 | 0.30 | 0.30 |
| Piperonyl Butoxide | — | 1 | 1 | — | 1 | 1 | — | — |
| Kathon 893* | — | — | — | — | — | — | 0.20 | 0.20 |
| Wocosin 50TK** | — | — | — | — | — | — | — | — |
| Water-Based Microemulsion | | | | | | | | |
| Water | 94 | | | | | | 92 | 94 |
| | 100 | 100 | 100 | 100 | 100 | 100 | 100 | 100 |
| Properties of Aqueous Microemulsion | | | | | | | | |
| at RT | clear | clear | clear | | | | | |
| at 0° C. | | | | | | | | |
| 0 hr. | clear | clear | clear | clear | clear | | clear | |
| 24 hr. | cloudy | clear | — | | | | | |
| 5 days | milky | clear | | clear | clear | | clear | |
| Upon warming to 45° and | clear | clear | | | | | | |
| for 3 storing days | | | | | | | | |
| cooling to RT | cloudy to clear | | | | | | | |

*2N-octyl-4-isothiazolin-3-one
**50% solution of propaconazole in propylene glycol While the invention has been described with particular reference to certain embodiments thereof, it will be understood that changes and modifications may be made which are within the skill of the art. Accordingly, it is intended to be bound only by the following claims, in which:

What is claimed is:

1. An inert matrix composition for forming a clear, efficacious aqueous microemulsion upon admixture with a predetermined amount of a pyrethroid insecticide and water, which is stable at or below room temperature for an extended period of time, consisting essentially of a predetermined mixture of nonionic surfactants:
   (a) a $C_6$-$C_{18}$ alkylpyrrolidone,
   (b) an alkyl phenol ethoxylated alcohol with HLB≧6; and
   (c) an ethylene oxide/propylene oxide/ethylene oxide block copolymer,
in a weight ratio of (a):(b):(c) of about 0.5-2:0.5-2:3-12.

2. An inert matrix composition according to claim 1 which includes up to 60% by weight thereof of N-methylpyrrolidone.

3. An inert matrix composition according to claim 1 wherein (b) is a nonylphenol ethoxylated alcohol with 9 ethylene oxide groups.

4. An inert matrix composition according to claim 1 which includes an anionic surfactant.

5. An inert matrix composition according to claim 4 in which said anionic surfactant is a nonylphenol ethoxylated phosphate ester with 9 ethylene oxide groups.

6. A two-part microemulsion system for forming a clear, efficacious, aqueous microemulsion of a pyrethroid insecticide by admixture of the respective parts of said system, and water, which is stable at or below room temperature for an extended period of time, consisting essentially of:
   (i) as one part, the inert matrix composition of claim 1, and
   (ii) as the second part, a powdered pyrethroid insecticide, optionally including a synergist or another active agricultural ingredient, or both.

7. A system according to claim 6 wherein said system includes up to 60% by weight of N-methylpyrrolidone as cosolvent in which said N-methylpyrrolidone is present in either one or both parts of said system.

8. A microemulsion concentrate for forming a clear, efficacious aqueous microemulsion of a pyrethroid insecticide upon dilution with water, which is stable at or below room temperature for an extended period of time, consisting essentially of:
   about 5-20% of a $C_6$-$C_{18}$ alkylpyrrolidone,
   about 30-72% of an alkyl phenol ethoxylated alcohol with HLB≧6,
   about 5-20% of an ethylene oxide/propylene oxide/ethylene oxide block copolymer, and
   about 0.5-20% of a pyrethroid insecticide, by weight of said concentrate.

9. A microemulsion concentrate according to claim 8 which includes about 4-6% of N-methylpyrrolidone.

10. A clear, efficacious, aqueous microemulsion of a pyrethroid insecticide which is stable at or below room temperature for an extended period of time consisting essentially of:
    about 0.5-20 parts of the microemulsion concentrate of claim 8, and
    about 80-99.5 parts of water.

11. A clear, efficacious, aqueous microemulsion according to claim 10 which includes about 4-60% of N-methylpyrrolidone.

* * * * *